(12) United States Patent
Kuramoto

(10) Patent No.: US 9,918,060 B2
(45) Date of Patent: Mar. 13, 2018

(54) ENDOSCOPE SYSTEM AND OPERATING METHOD THEREOF

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 360 days.

(21) Appl. No.: 14/626,705

(22) Filed: Feb. 19, 2015

(65) Prior Publication Data

US 2015/0245002 A1   Aug. 27, 2015

(30) Foreign Application Priority Data

Feb. 27, 2014 (JP) ................. 2014-036856

(51) Int. Cl.
| | |
|---|---|
| H04N 9/73 | (2006.01) |
| H04N 9/64 | (2006.01) |
| G02B 23/24 | (2006.01) |
| A61B 1/00 | (2006.01) |
| A61B 1/06 | (2006.01) |
| H05B 33/08 | (2006.01) |

(52) U.S. Cl.
CPC ......... *H04N 9/646* (2013.01); *A61B 1/00009* (2013.01); *A61B 1/0638* (2013.01); *G02B 23/2461* (2013.01); *H04N 9/735* (2013.01); *H05B 33/086* (2013.01); *A61B 1/0684* (2013.01)

(58) Field of Classification Search
CPC . A61B 1/00009; A61B 1/0638; A61B 1/0684; G02B 23/2461; H04N 9/646; H04N 9/735; H05B 33/086
See application file for complete search history.

(56) References Cited

U.S. PATENT DOCUMENTS

| | | | |
|---|---|---|---|
| 6,600,833 B1 * | 7/2003 | Tan ...................... | H04N 1/6016 348/612 |
| 2008/0249368 A1 * | 10/2008 | Takei ................. | A61B 1/00009 600/178 |
| 2009/0122135 A1 * | 5/2009 | Matsui .................. | A61B 1/045 348/65 |

(Continued)

FOREIGN PATENT DOCUMENTS

JP    2002-122794 A    4/2002

*Primary Examiner* — Mohammed Rahaman
(74) *Attorney, Agent, or Firm* — Birch, Stewart, Kolasch & Birch, LLP

(57) ABSTRACT

A light source unit emits multi-colored light. The amount of light of each color is controlled so that the multi-colored light has a first light emission ratio. A color image sensor images an object and outputs a multi-colored image signal. Again coefficient calculator calculates provisional gain coefficients based on the multi-colored image signal. A noise evaluation value calculator calculates a noise evaluation value based on the provisional gain coefficients and set color correction coefficients. A judging section judges whether or not the noise evaluation value is an allowance or less. In a case where the noise evaluation value is judged to be the allowance or less, a coefficient determiner determines the provisional gain coefficients as set gain coefficients, and a light emission ratio determiner determines the first light emission ratio of the multi-colored light as a set light emission ratio.

8 Claims, 7 Drawing Sheets

(56) References Cited

U.S. PATENT DOCUMENTS

2011/0069162 A1\* 3/2011 Ozawa ............... A61B 1/00057
 348/68
2012/0116159 A1\* 5/2012 Mizuyoshi ........... A61B 1/0653
 600/109

\* cited by examiner

ENDOSCOPE SYSTEM AND OPERATING METHOD THEREOF

CROSS-REFERENCE TO RELATED APPLICATIONS

The present application claims priority under 35 U.S.C. § 119 to Japanese Patent Application No. 2014-036856 filed on Feb. 27, 2014. The above application is hereby expressly incorporated by reference, in its entirety, into the present application.

BACKGROUND OF THE INVENTION

1. Field of the Invention

The present invention relates to an endoscope system that illuminates the inside of a body cavity using a plurality of semiconductor light sources such as LEDs, and an operating method thereof.

2. Description Related to the Prior Art

In a medical field, diagnosis using an endoscope system having a light source unit, an endoscope, and a processor device is widely carried out. The endoscope is generally provided with a color image sensor, which images an observation object and outputs an image signal of a plurality of colors (a multi-colored image signal). Since the difference among the image sensors varies the spectral sensitivity of the endoscopes, it is known that the variations in the spectral sensitivity cause color variations among endoscopic images.

As a method for eliminating such color variations among the endoscopic images, there is a method by which whenever exchanging the endoscope, a white reference object is imaged with the color image sensor and the multi-colored image signal is obtained. Then, a gain process is applied thereto by multiplying an image signal of each color by a gain coefficient such that the multi-colored image signal attains a predetermined balance, in order to adjust white balance of the endoscopic image. Also, provided that the light source unit includes a plurality of semiconductor light sources that can emit light of three colors i.e. red light, green light, and blue light in such a manner as to independently control individual light amounts, as described in Japanese Patent Laid-Open Publication No. 2002-122794, there is another method for adjusting the white balance of the endoscopic image by which the amount of light of each color is controlled such that the multi-colored image signal, which is obtained by imaging the white reference object with the color image sensor, attains the predetermined balance.

Here, if the image sensor is an RGB color sensor having favorable color separability in which light of different colors is hard to mix in pixels of a certain color (for example, a sensor in which blue light and red light are hardly mixed in G pixels), the white balance can be adjusted just by independently controlling the amount of light of each color, without increasing the gain coefficients of the gain process. Not increasing the gain coefficients minimizes noise.

On the other hand, in a case where the image sensor has poor color separability in which light of different colors is easy to mix in pixels of a certain color (for example, a sensor in which blue light and red light are easily mixed in G pixels), the adjustment of the white balance just by controlling the amount of light of each color disturbs the balance among the amounts of light of individual colors. Taking a case where G pixels are sufficiently sensitive to blue light and red light (see FIG. 5) as an example, adjusting the white balance just by controlling the amount of light of each color makes the amount of green light smaller than the amounts of the blue light and the red light, as shown by a solid line in FIG. 10. Note that, in FIG. 10, the solid line represents relative radiant intensity of the blue light, the green light, and the red light after the adjustment of the white balance by the light amount control. A dashed line represents default relative radiant intensity of the blue light, the green light, and the red light.

As described above, in a case where the amount of the green light becomes smaller than the amounts of the blue light and the red light, color may not be correctly displayed in the image. Accordingly, a color correction matrix process is applied with the aim of correctly displaying the color of the image. In this case, however, color correction coefficients (especially, a color correction coefficient for correcting a green component) used in the color correction matrix process become high. The high color correction coefficients increase noise.

SUMMARY OF THE INVENTION

An object of the present invention is to provide an endoscope system that can suppress noise even with the use of a color image sensor of poor color separability, and an operating method thereof.

To achieve the above and other objects, an endoscope system according to the present invention includes a light source unit, a color correction matrix processor, and a determining unit. The light source unit emits multi-colored light having a set light emission ratio in a specific observation mode. The color correction matrix processor performs a color correction matrix process by using a set color correction coefficient. The determining unit determines the set light emission ratio such that a noise evaluation value calculated based on at least the set color correction coefficient becomes an allowance or less. It is preferable that the endoscope system further include a white balance processor for performing a white balance process by using a set gain coefficient. The determining unit preferably determines the set gain coefficient such that the noise evaluation value becomes the allowance or less.

It is preferable that the endoscope system further include a light source controller, an endoscope, and image signal storage. The light source controller controls the amount of light of each color so that the multi-colored light has a first light emission ratio. The endoscope has a color image sensor for imaging an object and outputting a multi-colored image signal. The image signal storage stores a first multi-colored image signal obtained by imaging with the color image sensor a reference object irradiated with the multi-colored light having the first light emission ratio. The determining unit preferably includes a gain coefficient calculator, a noise evaluation value calculator, a judging section, a coefficient determiner, and a light emission ratio determiner. The gain coefficient calculator calculates a provisional gain coefficient based on the first multi-colored image signal. The noise evaluation value calculator calculates the noise evaluation value based on the provisional gain coefficient and the set color correction coefficient. The judging section judges whether or not the noise evaluation value is the allowance or less. The coefficient determiner determines the provisional gain coefficient used in calculating the noise evaluation value that the judging section judges to be the allowance or less, as the set gain coefficient. The light emission ratio determiner determines the first light emission ratio of the multi-colored light used in calculating the noise evaluation value that the judging section judges to be the allowance or less, as the set light emission ratio.

It is preferable that the endoscope system further include a modification controller. The modification controller controls the light source controller, the gain coefficient calculator, and the noise evaluation value calculator, such that in a case where the judging section judges that the noise evaluation value exceeds the allowance, the first light emission ratio of the multi-colored light is modified and the provisional gain coefficient and the noise evaluation value are calculated from the first multi-colored image signal obtained based on the modified first light emission ratio.

The noise evaluation value is preferably increased with increase in the provisional gain coefficient or the set color correction coefficient. The multi-colored light preferably includes red light, green light, and blue light, and the multi-colored image signal is preferably an RGB image signal. The multi-colored light preferably includes first narrow band light in a violet band or a blue band and second narrow band light in a green band, and the multi-colored image signal is preferably an RGB image signal. Out of the RGB image signal, a G image signal preferably has information about light in a band other than the green band of the multi-colored light.

In the above-described endoscope system according to the present invention, the light source controller controls the amount of light of each color so that the multi-colored light has a second light emission ratio. It is preferable that the endoscope system further include a color correction coefficient calculator for calculating the set color correction coefficient from a second multi-colored image signal, which is obtained by imaging with the color image sensor the reference object irradiated with the multi-colored light having the second light emission ratio.

A method for operating an endoscope system according to the present invention includes the steps of emitting multi-colored light having a set light emission ratio from a light source unit in a specific observation mode; performing a color correction matrix process by a color correction matrix processor by using a set color correction coefficient; and determining the set light emission ratio by a determining unit such that a noise evaluation value calculated based on at least the set color correction coefficient becomes an allowance or less. The determining unit preferably determines a set gain coefficient used in a white balance process such that the noise evaluation value becomes the allowance or less.

It is preferable that the method further include the steps of controlling the amount of light of each color by a light source controller so that the multi-colored light has a first light emission ratio; storing to image signal storage a first multi-colored image signal obtained by imaging with a color image sensor a reference object irradiated with the multi-colored light having the first light emission ratio; calculating a provisional gain coefficient by a gain coefficient calculator from the first multi-colored image signal; calculating a noise evaluation value by a noise evaluation value calculator on the basis of the provisional gain coefficient and the set color correction coefficient: judging by a judging section whether or not the noise evaluation value is the allowance or less; determining by a coefficient determiner the provisional gain coefficient used in calculating the noise evaluation value that the judging section judges to be the allowance or less, as the set gain coefficient; and determining by a light emission ratio determiner the first light emission ratio of the multi-colored light used in calculating the noise evaluation value that the judging section judges to be the allowance or less, as the set light emission ratio.

Moreover, an endoscope system according to the present invention includes a light source unit, a color correction matrix processor, a light source controller, a noise evaluation value calculator, a judging section, and a light emission ratio determiner. The light source unit emits multi-colored light having a set light emission ratio in a specific observation mode. The color correction matrix processor performs a color correction matrix process by using a set color correction coefficient. The light source controller controls the amount of light of each color so that the multi-colored light has a first light emission ratio. The noise evaluation value calculator calculates a noise evaluation value based on at least the set color correction coefficient. The judging section judges whether or not the noise evaluation value is an allowance or less. The light emission ratio determiner determines the first light emission ratio of the multi-colored light used in calculating the noise evaluation value that the judging section judges to be the allowance or less, as the set light emission ratio.

According to the present invention, it is possible to suppress noise even with the use of a color image sensor having poor color separability.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

First Embodiment

Figure 1:
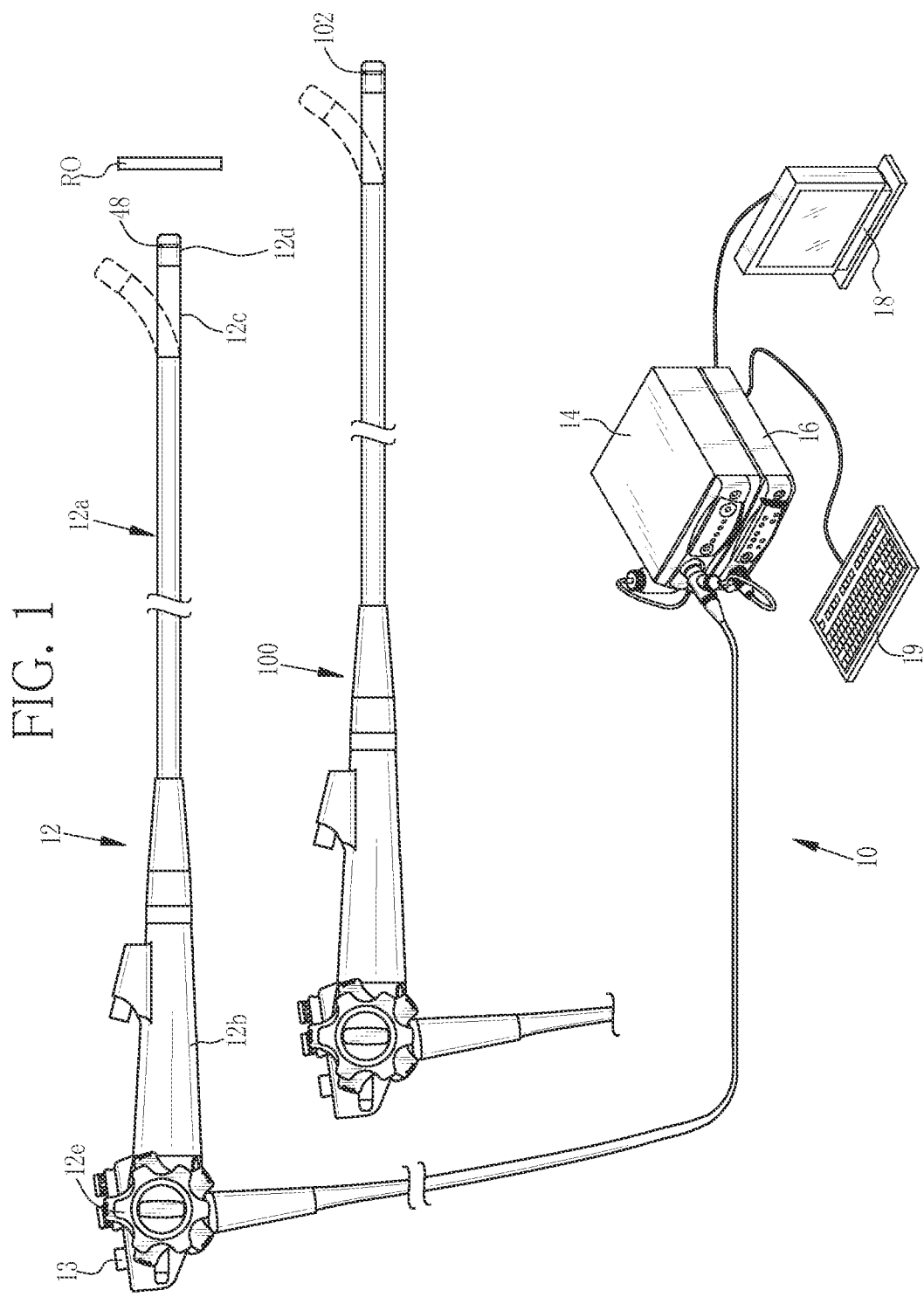
FIG. 1 is a perspective view of an endoscope system.

As shown in FIG. 1, an endoscope system 10 according to a first embodiment includes an endoscope 12, a light source unit 14, a processor device 16, a monitor 18, and a console 19. The endoscope 12 is optically connected to the light source unit 14, and electrically connected to the processor device 16. The processor device 16 has an insert section 12a to be introduced into a body cavity, a handling section 12b provided at a proximal end of the insert section 12a, and a bending section 12c and a distal end portion 12d provided at a distal end of the insert section 12a. The bending section 12c is bent by operation of an angle knob 12e of the handling section 12b. The bending operation aims the distal end portion 12d at a desired direction.

The handling section 12b is provided with a mode change switch 13, in addition to the angle knob 12e. The mode change switch 13 is used for switching among three types of modes, that is, a normal observation mode, a special observation mode, and a first calibration mode. In the normal observation mode (a specific observation mode), a normal light image is displayed on the monitor 18 by using white light. In the special observation mode (another specific observation mode), a special light image is displayed on the monitor 18 by using light of a specific wavelength that can highlight specific structure such as superficial blood vessels with contrast difference from mucosa. In the first calibration mode, are determined set light emission ratios of light of a plurality of colors (multi-colored light) to be used in the normal observation mode and the special observation mode, and set gain coefficients to be used in a white balance process in the normal observation mode and the special observation mode.

To the light source unit 14 and the processor device 16, an endoscope 100 different from the endoscope 12 is connectable. The endoscopes 12 and 100 have similar structure, but an image sensor 48 of the endoscope 12 has different spectral characteristics from an image sensor 102 of the endoscope 100. Thus, the connection of the endoscope 12 or 100 requires calibration of white balance by switching to the first calibration mode with the mode change switch 13. Note that, exchange of the endoscope may automatically switch to the first calibration mode and determine the set light emission ratios and the set gain coefficients.

The processor device 16 is electrically connected to the monitor 18 and the console 19. The monitor 18 outputs and displays image information and the like. The console 19 functions as a user interface (UI) for receiving input operation of function setting and the like. Note that, an external recorder (not shown) for recording the image information and the like may be connected to the processor device 16.

Figure 2:
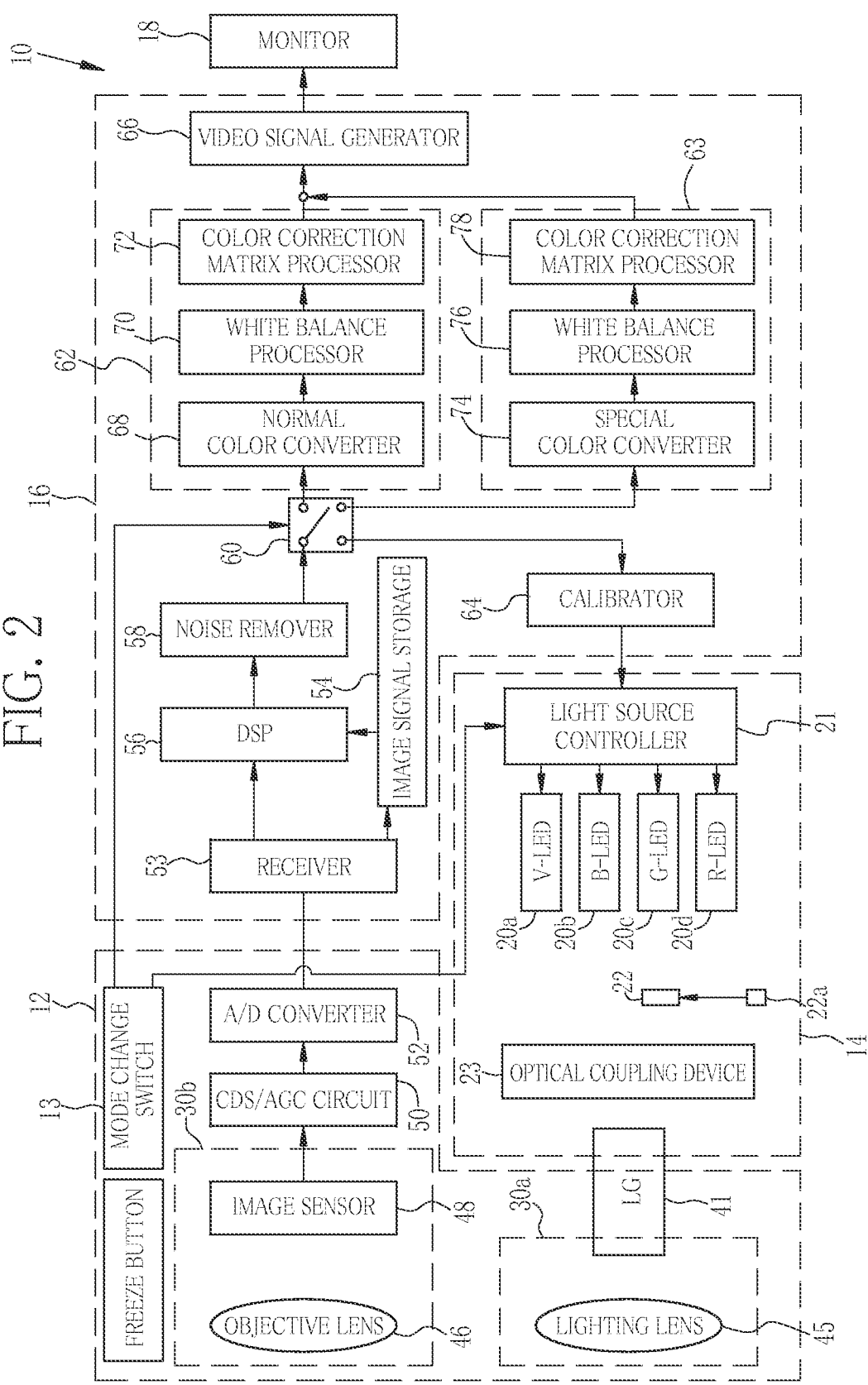
FIG. 2 is a block diagram of the endoscope system.

As shown in FIG. 2, the light source unit 14 includes a violet light emitting diode (V-LED) 20a, a blue light emitting diode (B-LED) 20b, a green light emitting diode (G-LED) 20c, a red light emitting diode (R-LED) 20d, a light source controller 21 for controlling the operation of the LEDs 20a to 20d of four colors (a light source unit), a green narrow band filter 22 inserted into and retracted from an optical axis of the G-LED 20c, and an optical coupling device 23 for coupling optical axes of light emitted from the LEDs 20a to 20d of the four colors. The light coupled by the optical coupling device 23 is applied to the inside of the body cavity through a light guide 41, which extends through the insert section 12a, and a lighting lens 45. Note that, laser diodes (LDs) may be used instead of the LEDs. The green narrow band filter 22 is inserted and retracted by a filter inserting and removing device 22a.

The V-LED 20a produces violet light V having a center wavelength of 405 nm and a wavelength range of 380 to 420 nm. The B-LED 20b produces blue light B having a center wavelength of 460 nm and a wavelength range of 420 to 500 nm. The G-LED 20c produces green light G of normal distribution having a wavelength range of 480 to 600 nm. The R-LED 20d produces red light R having a center wavelength of 620 to 630 nm and a wavelength range of 600 to 650 nm. The green narrow band filter 22 passes green narrow band light Gn of 530 to 550 nm, out of the green light G emitted from the G-LED 20c.

Figure 3:
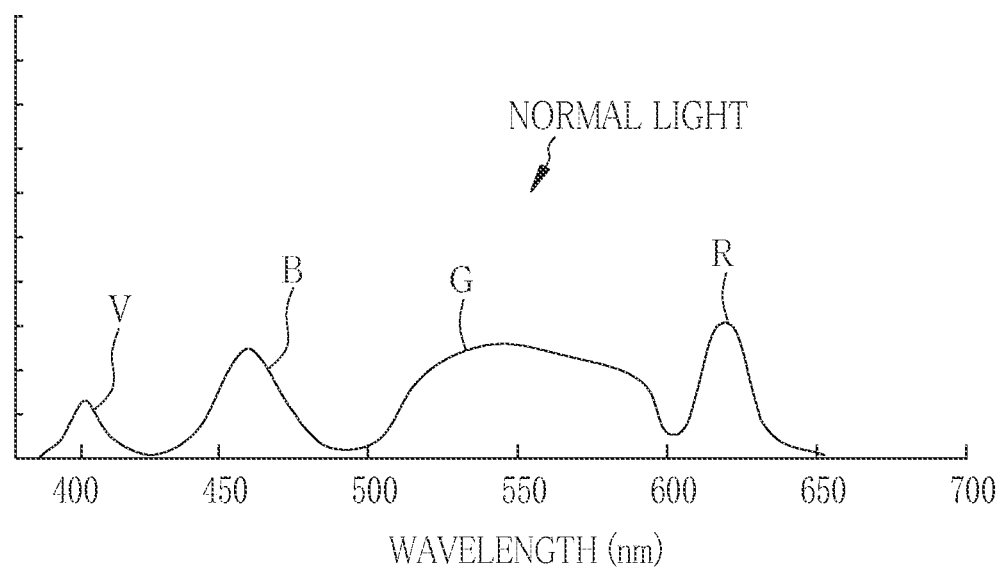
FIG. 3 is a graph showing an emission spectrum of normal light.

In the normal observation mode, the light source controller 21 turns on all of the V-LED 20a, the B-LED 20b, the G-LED 20c, and the R-LED 20d in a state of retracting the green narrow band filter 22 from the optical axis of the G-LED 20c. Thereby, as shown in FIG. 3, mixture of the light of the four colors, that is, the violet light V, the blue light B, the green light G, and the red light R produces normal light. The violet light V, the blue light B, the green light G, and the red light R are emitted at the set light emission ratio. This set light emission ratio is determined by a light emission ratio determiner 87 (see FIG. 6). Note that, in the normal observation mode, light of three colors, i.e. the blue light B, the green light G, and the red light R may be emitted.

Figure 4:
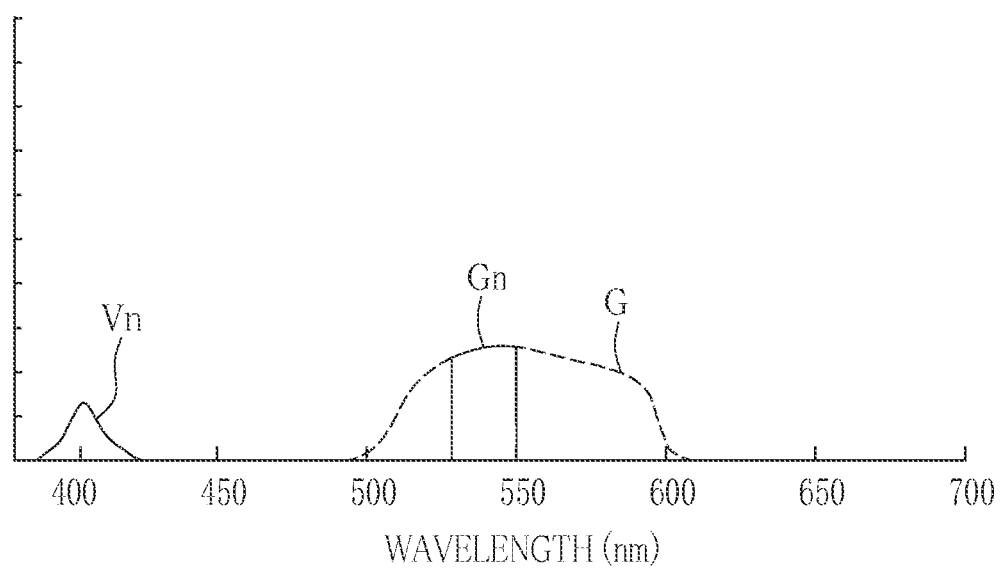
FIG. 4 is a graph showing emission spectra of violet light V and green narrow band light Gn.

In the special observation mode, on the other hand, the V-LED 20a and the G-LED 20c are turned on simultaneously in a state of inserting the green narrow band filter 22 into the optical axis of the G-LED 20c, to produce the violet light V (first narrow band light) and the green narrow band light Gn (second narrow band light) at the same time. Accordingly, as shown in FIG. 4, the violet light V from the V-LED 20a and the green narrow band light Gn having a wavelength narrowed by the green narrow band filter 22 are produced at the same time. The violet light V and the green narrow band light Gn are emitted at the set light emission ratio. This set light emission ratio is determined by the light emission ratio determiner 87 (see FIG. 6). Note that, in the special observation mode, blue narrow band light may be emitted as the first narrow band light, instead of the violet light V.

In the first calibration mode, the light source controller 21 controls each of the LEDs 20a to 20d so as to perform calibration light emission for normal observation and calibration light emission for special observation. In the calibration light emission for the normal observation, all of the V-LED 20a, the B-LED 20b, the G-LED 20c, and the R-LED 20d are turned on in a state of retracting the green narrow band filter 22 from the optical axis of the G-LED 20c, so that the light of the four colors, including the violet light V, the blue light B, the green light G, and the red light R is emitted. Also, in the calibration light emission for the normal observation, the violet light V, the blue light B, the green light G, and the red light R are emitted at a first light emission ratio for the normal observation.

In the calibration light emission for the special observation, on the other hand, the V-LED 20a and the G-LED 20c are turned on simultaneously in a state of inserting the green narrow band filter 22 into the optical axis of the G-LED 20c, so that the violet light V and the green narrow band light Gn are produced at the same time. Also, in the calibration light emission for the special observation, the violet light V and the green narrow band light Gn are emitted at a first light emission ratio for the special observation.

The light guide 41, which is contained in the endoscope 12 and a universal cord (a cord for connecting the endoscope 12 to the light source unit 14 and the processor device 16), transmits the light coupled by the optical coupling device 23 to the distal end portion 12d of the endoscope 12. Note that, a multi-mode fiber is usable as the light guide 41. As an example, a slender fiber cable having a core diameter of 105 μm, a cladding diameter of 125 μm, and a diameter ϕ, including a protective layer being a sheath, of 0.3 to 0.5 mm is usable.

The distal end portion 12d of the endoscope 12 is provided with a lighting optical system 30a and an imaging optical system 30b. The lighting optical system 30a has the lighting lens 45. The light from the light guide 41 is applied through the lighting lens 45 to an object to be observed. The lighting optical system 30b has an objective lens 46 and the image sensor 48. The light reflected from the object is incident upon the image sensor 48 through the objective lens 46. Thus, the image sensor 48 forms a reflected image of the object. Note that, in the normal observation mode and the special observation mode, the light is applied to the inside of the body cavity e.g. an esophagus, a stomach, or a large intestine, and the image sensor 48 captures the reflected image thereof. In the first calibration mode, on the other hand, the light is applied to a white reference object RO (see FIG. 1), and the image sensor 48 captures the reflected image thereof.

The image sensor 48 is a color image sensor, which captures the reflected image of the object and outputs an image signal (multi-colored image signal). This image sensor 48 is preferably a charge coupled device (CCD) image sensor, a complementary metal-oxide semiconductor (CMOS) image sensor, or the like. The image sensor 48 used in the present invention is a color image sensor for obtaining an RGB image signal of three colors of R (red), G (green), and B (blue), in other words, a so-called RGB image sensor provided with R pixels having an R filter, G pixels having a G filter, and B pixels having a B filter.

Figure 5:
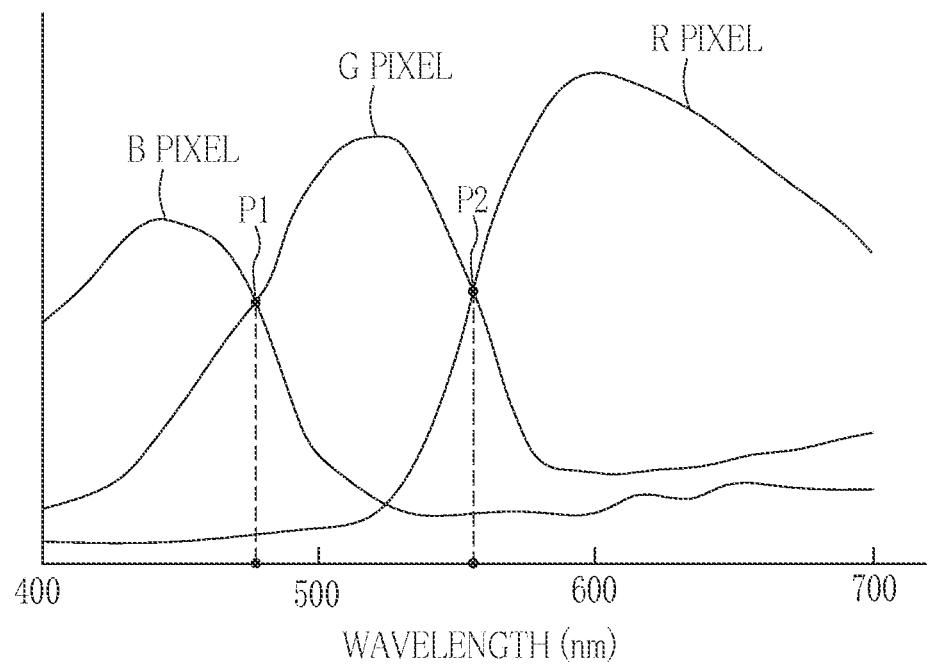
FIG. 5 is a graph showing the spectral sensitivity of a B pixel, a G pixel, and an R pixel of an image sensor.

The case of using the image sensor 48 having the G pixels that are sensitive to not only a green band but also a blue band and a red band, as shown in FIG. 5, is taken as an example. In the normal observation mode, the violet light V, the blue light B, and the red light R are incident upon the G pixels, in addition to the green light G. In the special observation mode, the violet light V is incident upon the G pixels, in addition to the green narrow band light Gn. Therefore, since the G pixels cannot certainly achieve color separation, the image sensor 48 is a sensor of poor color separability. On the other hand, in the case of using the image sensor 48 having the G pixels that are hardly sensitive to the blue band and the green band, light is hardly incident upon the G pixels, except for light in the green band including the green light G, the green narrow band light Gn, and the like. Therefore, the G pixels can certainly achieve color separation.

Note that, the color separability of the pixel of each color in the image sensor 48 is defined by a color mixture ratio, which represents a ratio of mixture of other colors in the pixel of each color. For example, the color mixture ratio of the G pixel is represented by $(S2+S3)/S1$, wherein in FIG. 5, S1 represents the size of an entire area in which the G pixel is sensitive, and S2 represents the size of a part of the area on a short wavelength side relative to a cross point P1 at which the sensitivity of the G pixel coincides with that of the B pixel, and S3 represents the size of another part of the area on a long wavelength side relative to a cross point P2 at which the sensitivity of the G pixel coincides with that of the R pixel. The color mixture ratios of the B pixel and the R pixel can be defined in a like manner.

As shown in FIG. 2, the image signal outputted from the image sensor 48 is sent to a CDS/AGC circuit 50. The CDS/AGC circuit 50 applies correlated double sampling (CDS) and auto gain control (AGC) to the image signal, being an analog signal. The image signal passed through the CDS/AGC circuit 50 is converted into a digital image signal by an analog-to-digital converter (A/D converter) 52. The converted digital image signal is inputted to the processor device 16.

The processor device 16 is provided with a receiver 53, image signal storage 54, a digital signal processor (DSP) 56, a noise remover 58, an image processing switching section 60, a normal light image processing unit 62, a special light image processing unit 63, a calibrator (a determining unit) 64, and a video signal generator 66. The receiver 53 receives the digital RGB image signal from the endoscope 12. Out of the RGB image signal, an R image signal corresponds to signals outputted from the R pixels of the image sensor 48. The G image signal corresponds to signals outputted from the G pixels of the image sensor 48. The B image signal corresponds to signals outputted from the B pixels of the image sensor 48. In the case of using the image sensor 48 having the G pixels that are sensitive to not only the green band but also the blue band and the red band, the G image signal contains information about light in the bands (the blue band and the red band) other than the green band. This RGB image signal is sent to the DSP 56.

Note that, in the first calibration mode, the RGB image signal from the receiver 53 is sent to the DSP 56 after being stored to the image signal storage 54. The image signal storage 54 stores the RGB image signal in associated with a scope ID of the endoscope. Since the RGB image signal obtained in the first calibration mode is stored in associated with each scope ID, as described above, in exchanging the endoscope at the next time, it is possible to determine the set light emission ratios and the set gain coefficients without imaging the reference object.

The DSP 56 applies a gamma correction process and a color correction process to the RGB image signal. The noise remover 58 applies a noise removal process (for example, a method of moving averages, a median filtering method, or the like) to the RGB image signal after being subjected to the gamma correction and the like by the DSP 56, to remove noise. The RGB image signal after the noise removal is sent to the image processing switching section 60.

In a case where the endoscope system 10 is put in the normal observation mode with the operation of the mode change switch 13, the image processing switching section 60 sends the RGB image signal to the normal light image processing unit 62. In the special observation mode, the image processing switching section 60 sends the RGB image signal to the special light image processing unit 63. In the first calibration mode, the image processing switching section 60 sends the RGB image signal to the calibrator 64.

The normal light image processing unit 62, which has a normal color converter 68, a white balance processor 70, and a color correction matrix processor 72, produces a normal light image in which the inside of the body cavity is represented with color of a normal living body. The normal color converter 68 applies a color conversion process to the RGB image signal, and outputs a color-converted RGB image signal. A color-converted R image signal corresponds to the R image signal before the color conversion process. A color-converted G image signal corresponds to the G image signal before the color conversion process. A color-converted B image signal corresponds to the B image signal before the color conversion process.

The white balance processor 70 applies a white balance process to the color-converted RGB image signal, and outputs a white-balanced RGB image signal. The white balance process is performed by a matrix operation of the following expression (1). A white-balanced R image signal "Ry" is obtained by multiplying the color-converted R image signal (represented as "Rx") by a set gain coefficient "Gain R" for the normal observation. Also, a white-balanced G image signal "Gy" is obtained by multiplying the color-converted G image signal (represented as "Gx") by a set gain coefficient "Gain G" for the normal observation. A white-balanced B image signal "By" is obtained by multiplying the color-converted B image signal (represented as "Bx") by a set gain coefficient "Gain B" for the normal observation.

$$\begin{bmatrix} Ry \\ Gy \\ By \end{bmatrix} = \begin{bmatrix} GainR & 0 & 0 \\ 0 & GainG & 0 \\ 0 & 0 & GainB \end{bmatrix} \times \begin{bmatrix} Rx \\ Gx \\ Bx \end{bmatrix} \quad \text{Expression (1)}$$

The color correction matrix processor 72 applies a color correction matrix process to the white-balanced RGB image signal, and outputs a color-correction-matrix-processed RGB image signal. The color correction matrix process is performed by a matrix operation of the following expression (2). The color-correction-matrix-processed RGB image signal is inputted to the video signal generator 66.

$$\begin{bmatrix} Rz \\ Gz \\ Bz \end{bmatrix} = \begin{bmatrix} C_{00} & C_{01} & C_{02} \\ C_{10} & C_{11} & C_{12} \\ C_{20} & C_{21} & C_{22} \end{bmatrix} \times \begin{bmatrix} Ry \\ Gy \\ By \end{bmatrix} \quad \text{Expression (2)}$$

In the expression (2), "Rz" represents a color-correction-matrix-processed R image signal. "Gz" represents a color-correction-matrix-processed G image signal. "Bz" represents a color-correction-matrix-processed B image signal. "$C_{00}$", "$C_{01}$", "$C_{02}$", "$C_{10}$", "$C_{11}$", "$C_{12}$", "$C_{20}$", "$C_{21}$", and "$C_{22}$" represent the set color correction coefficients for the normal observation.

The special light image processing unit 63, which has a special color converter 74, a white balance processor 76, and a color correction matrix processor 78, produces a special light image in which the specific structure such as the superficial blood vessels or the like is emphasized. The special color converter 74 applies a color conversion process to the RGB image signal of three colors, and outputs a color-converted RGB image signal. A color-converted R image signal corresponds to the R image signal before the color conversion process. A color-converted G image signal corresponds to the G image signal before the color conversion process. A color-converted B image signal corresponds to the B image signal before the color conversion process. Note that, in the special observation mode, almost no light is incident upon the R pixels of the image sensor 48, so the color-converted R image signal has a pixel value of almost "0".

The white balance processor 76 applies a white balance process to the color-converted RGB image signal, and outputs a white-balanced RGB image signal. The white balance process is performed in the same manner as the white balance process (the matrix operation by the expression (1)) of the white balance processor 70, with the use of set gain coefficients "Gain R", "Gain G", and "Gain B" for the special observation.

The color correction matrix processor 78 applies a color correction matrix process to the white-balanced RGB image signal. The color correction matrix process is performed in the same manner as the color correction matrix process (the matrix operation by the expression (2)) of the color correction matrix processor 72, with the use of set color correction coefficients "$C_{00}$", "$C_{01}$", "$C_{02}$", "$C_{10}$", "$C_{11}$", "$C_{12}$", "$C_{20}$", "$C_{21}$", and "$C_{22}$" for the special observation.

The video signal generator 66 converts the RGB image signal inputted from the normal light image processing unit 62 or the special light image processing unit 63 into an RGB video signal, which is displayable on the monitor 18 as a full-color image. Out of the RGB image signal from the normal light image processing unit 62, the R image signal is assigned to an R video signal. The G image signal is assigned to a G video signal. The B image signal is assigned to a B video signal. Out of the RGB image signal from the special light image processing unit 63, the B image signal is assigned to the B video signal and the G video signal. The G image signal is assigned to the R video signal. The monitor 18 displays the normal light image in the normal observation mode, and the special light image in the special observation mode based on the RGB image signal.

Figure 6:
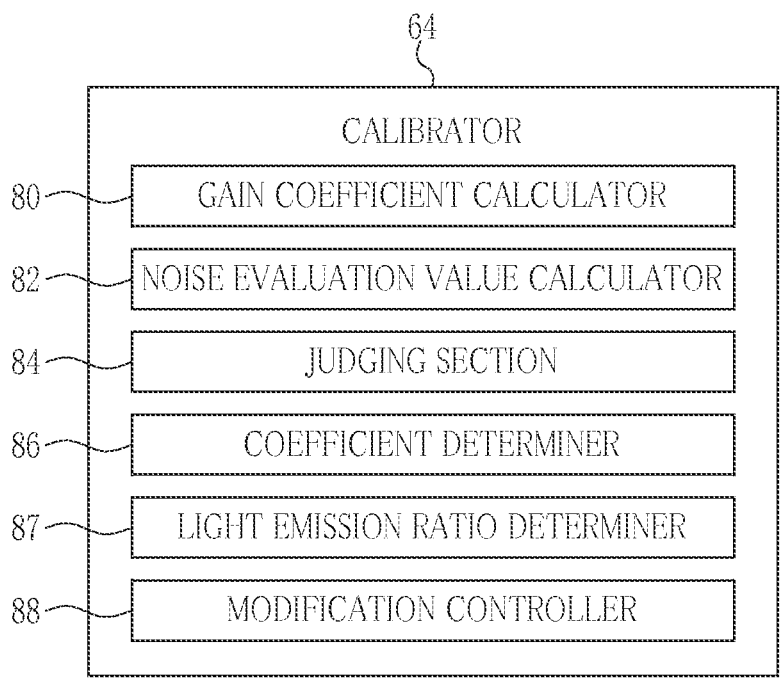
FIG. 6 is a block diagram of a calibrator according to a first embodiment.

As shown in FIG. 6, the calibrator 64 includes a gain coefficient calculator 80, a noise evaluation value calculator 82, a judging section 84, a coefficient determiner 86, a light emission ratio determiner 87, and a modification controller 88. The gain coefficient calculator 80 calculates provisional gain coefficients "Gain R", "Gain G", and "Gain B" for the normal observation based on the RGB image signal obtained at the time of the calibration light emission for the normal observation. The gain coefficient calculator 80 calculates the provisional gain coefficients "Gain R", "Gain G", and "Gain B" for the normal observation such that the ratio among the R image signal, the G image signal, and the B image signal satisfies 1:1:1. Also, the gain coefficient calculator 80 calculates provisional gain coefficients "Gain R", "Gain G", and "Gain B" for the special observation based on the RGB image signal obtained at the time of the calibration light emission for the special observation, by the same method as the calculation method of the provisional gain coefficients for the normal observation.

The noise evaluation value calculator 82 calculates noise evaluation values for the normal observation and the special observation based on the gain coefficients "Gain R", "Gain G", and "Gain B" for the normal observation and the special observation obtained by the gain coefficient calculator 80 and the set color correction coefficients "$C_{00}$", "$C_{01}$", "$C_{02}$", "$C_{10}$", "$C_{11}$", "$C_{12}$", "$C_{20}$", "$C_{21}$", and "$C_{22}$". Note that, in the first embodiment, the set color correction coefficients "$C_{00}$", "$C_{O2}$", "$C_{10}$", "$C_{11}$", "$C_{12}$", "$C_{20}$", "$C_{21}$", and "$C_{22}$" are set in advance in shipping from a factory. Note that, the noise evaluation values may be calculated from only the set color correction coefficients "$C_{00}$", "$C_{01}$", "$C_{02}$", "$C_{10}$", "$C_{11}$", "$C_{12}$", "$C_{20}$", "$C_{21}$", and "$C_{22}$".

The noise evaluation value for the normal observation is calculated from the following expression (3) or (4). A value obtained by the expression (3) corresponds to a value converted to a luminance amplification factor. A value obtained by the expression (4) corresponds to a value converted to the sum of an RGB amplification factor. Therefore, luminance or the RGB amplification factor is increased with increase in the noise evaluation value, and hence noise is increased. On the contrary, the luminance or the RGB amplification factor is decreased with decrease in the noise evaluation value, and hence noise is reduced. Note that, as is apparent from the expressions (3) and (4), the noise evaluation value is increased with increase in the provisional gain coefficients or the set color correction coefficients.

Noise evaluation value=

$0.299 \times \sqrt{(C_{00} \times \text{Gain}R)^2 + (C_{01} \times \text{Gain}G)^2 + (C_{02} \times \text{Gain}B)^2}$ $+0.587 \times \sqrt{(C_{10} \times \text{Gain}R)^2 + (C_{11} \times \text{Gain}G)^2 + (C_{12} \times \text{Gain}B)^2}$ $+0.114 \times \sqrt{(C_{20} \times \text{Gain}R)^2 + (C_{21} \times \text{Gain}G)^2 + (C_{22} \times \text{Gain}B)^2}$ Expression (3):

Noise evaluation value=

$$\sqrt{(C_{00} \times \text{Gain}R)^2 + (C_{01} \times \text{Gain}G)^2 + (C_{02} \times \text{Gain}B)^2}$$

$$+\sqrt{(C_{10} \times \text{Gain}R)^2 + (C_{11} \times \text{Gain}G)^2 + (C_{12} \times \text{Gain}B)^2}$$

$$+\sqrt{(C_{20} \times \text{Gain}R)^2 + (C_{21} \times \text{Gain}G)^2 + (C_{22} \times \text{Gain}B)^2} \quad \text{Expression (4):}$$

On the other hand, the noise evaluation value for the special observation is calculated from the following expression (5). A value obtained from the expression (5) corresponds to a value converted to the luminance amplification factor. Therefore, the luminance amplification factor is increased with increase in the noise evaluation value, and hence noise is increased. On the contrary, the luminance amplification factor is decreased with decrease in the noise evaluation value, and hence noise is reduced. Note that, it is apparent from the expression (5) that the noise evaluation value is increased with increase in the provisional gain coefficients or the set color correction coefficients.

Noise evaluation value=

$$0.299 \times \sqrt{(C_{10} \times \text{Gain}R)^2 + (C_{11} \times \text{Gain}G)^2 + (C_{12} \times \text{Gain}B)^2}$$

$$+(0.587+0.114) \times$$
$$\sqrt{(C_{20} \times \text{Gain}R)^2 + (C_{21} \times \text{Gain}G)^2 + (C_{22} \times \text{Gain}B)^2} \quad \text{Expression (5):}$$

The judging section 84 judges whether or not the noise evaluation values for the normal observation and the special observation are equal to or less than a predetermined allowance. In a case where the noise evaluation value for the normal observation is judged to be the allowance or less, the coefficient determiner 86 determines the provisional gain coefficients "Gain R", "Gain G", and "Gain B" for the normal observation that are used in calculating the noise evaluation value as the set gain coefficients "Gain R", "Gain G", and "Gain B" for the normal observation. The determined set gain coefficients "Gain R", "Gain G", and "Gain B" for the normal observation are sent to the white balance processor 70 and used in the white balance process. Also, the light emission ratio determiner 87 determines the first light emission ratio of the violet light V, the blue light B, the green light G, and the red light R used in calculating the noise evaluation value that is the allowance or less, as the set light emission ratio in the normal observation mode.

In a case where the noise evaluation value for the special observation is judged to be the allowance or less, the same procedure as the case of the normal observation is followed. Thereby, the set gain coefficients "Gain R", "Gain G", and "Gain B" for the special observation are determined, and the set light emission ratio for the special observation is determined. Note that, the judging section 84 makes the judgment based on whether or not the noise evaluation value is the allowance or less. Instead of this, the noise evaluation value may be calculated a plurality of times, and the provisional gain coefficients used in calculating the least noise evaluation value, out of the calculated noise evaluation values, may be determined as the set gain coefficients.

On the other hand, the judging section 84 judges that the noise evaluation value for the normal observation exceeds the allowance, the modification controller 88 controls the light source controller 21 so as to modify the first light emission ratio by increasing or decreasing the light amounts of the LEDs 20a to 20d of the four colors. For example, in a case where the first light emission ratio among the violet light V, the blue light B, the green light G, and the red light R before the modification is "V1:B1:G1:R1" and the amount of the green light G is intended to be increased, the first light emission ratio is modified to "V1:B1:G2:R1 (G2 is higher than G1)". Then, the reference object is imaged under irradiation with the calibration light emission for the normal observation based on the modified first light emission ratio, to obtain the RGB image signal again.

Then, the modification controller 88 controls the gain coefficient calculator 80 and the noise evaluation value calculator 82 to calculate the provisional gain coefficients and the noise evaluation value again based on the re-obtained RGB image signal. The judging section 84 makes a judgment based on the recalculated noise evaluation value. The recalculation of the noise evaluation value and the like are repeated until the noise evaluation value comes to be the allowance or less. On the other hand, in a case where the judging section 84 judges that the noise evaluation value for the special observation exceeds the allowance, the same procedure as in the case of judging that the noise evaluation value for the normal observation exceeds the allowance is carried out.

Figure 7:
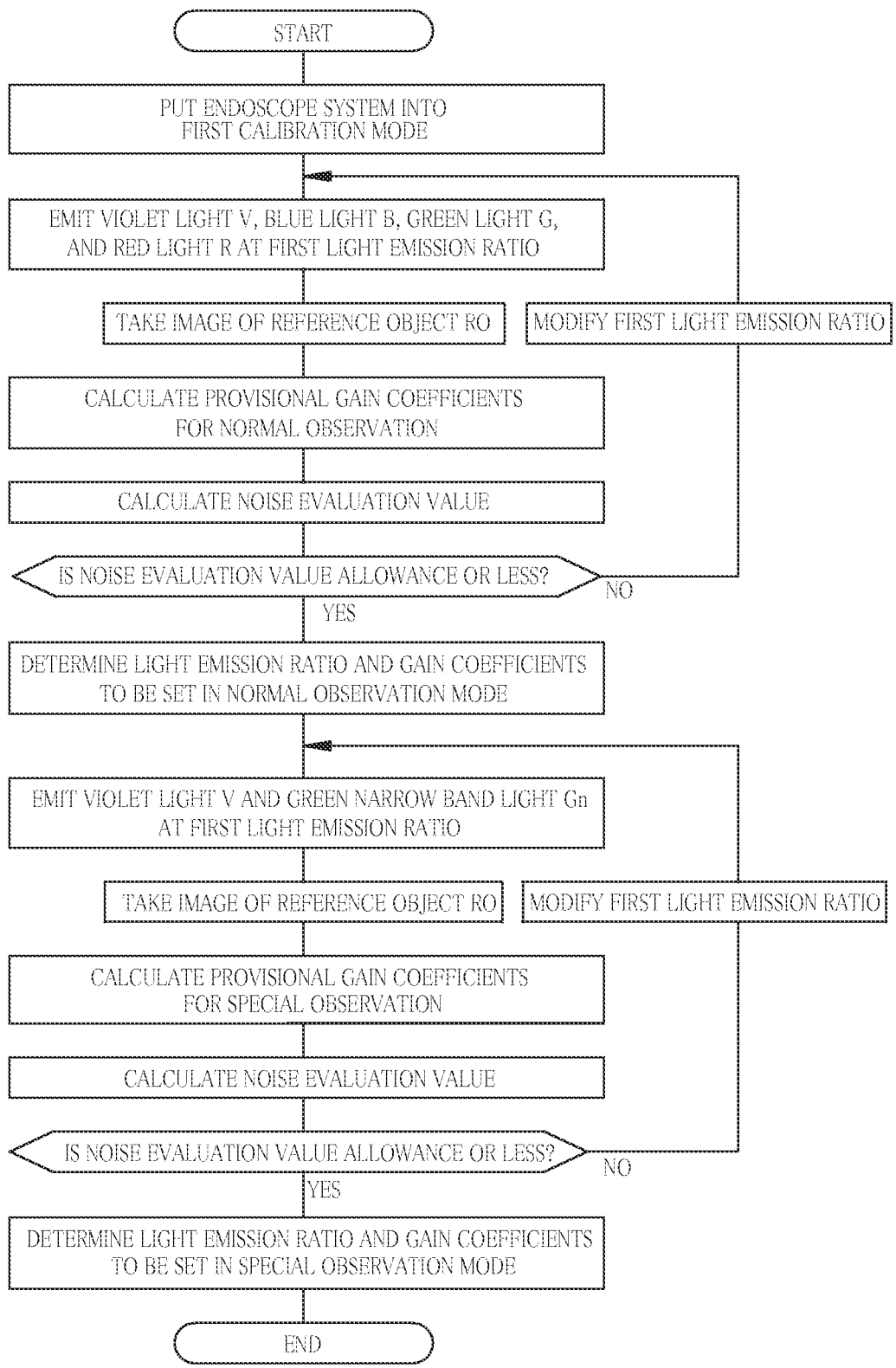
FIG. 7 is a flowchart showing a sequential flow of the present invention.

Next, the operation of the present invention will be described with referring to a flowchart of FIG. 7. First, the endoscope 12 is connected to the light source unit 14 and the processor device 16, and the distal end portion 12d of the endoscope 12 is aimed at the reference object RO. Then, the endoscope system 10 is put into the first calibration mode by the operation of the mode change switch 13. The calibration light emission for the normal observation is carried out by which the violet light V, the blue light B, the green light G, and the red light R are applied to the reference object RO at the first light emission ratio.

Then, the image sensor 48 images the reference object RO to obtain the RGB image signal. Based on this RGB image signal, the gain coefficient calculator 80 calculates the provisional gain coefficients "Gain R", "Gain G", and "Gain B" for the normal observation. After that, the noise evaluation value calculator 82 calculates the noise evaluation value based on the calculated provisional gain coefficients "Gain R", "Gain G", and "Gain B" and the set color correction coefficients "$C_{00}$", "$C_{01}$", "$C_{02}$", "$C_{10}$", "$C_{11}$", "$C_{12}$", "$C_{20}$", "$C_{21}$", and "$C_{22}$".

The judging section 84 judges whether or not the noise evaluation value is the allowance or less. In a case where the noise evaluation value is the allowance or less, the provisional gain coefficients for the normal observation used in calculating the noise evaluation value are determined as the set gain coefficients for the normal observation, and the first light emission ratio of the violet light V, the blue light B, the green light G, and the red light R used in calculating the noise evaluation value is determined as the set light emission ratio in the normal observation mode. On the other hand, in a case where the noise evaluation value exceeds the allowance, the first light emission ratio of the violet light V, the blue light B, the green light G, and the red light R is modified, and the provisional gain coefficients and the noise evaluation value are calculated again. This is repeated until the noise evaluation value comes to be the allowance or less.

After the set light emission ratio in the normal observation mode is determined and the set gain coefficients "Gain R", "Gain G", and "Gain B" for the normal observation are determined, the calibration light emission for the special observation is carried out to calculate and judge the noise evaluation value in the same manner as above. Thereby, the set light emission ratio of the violet light V and the green narrow band light Gn in the special observation mode is determined, and the set gain coefficients "Gain R", "Gain G", and "Gain B" for the special observation are determined.

Then, the first calibration mode is completed, and the endoscope system 10 is put into a state of readiness to properly perform endoscopy.

As described above, the set light emission ratio in the normal observation mode or the special observation mode is determined and the set gain coefficients "Gain R", "Gain G", and "Gain B" for the normal observation or the special observation are determined, such that the noise evaluation value becomes the allowance or less. Thereby, it is possible to minimize noise even with the use of the color image sensor having the poor color separability.

Second Embodiment

In the above first embodiment, the set color correction coefficients ("$C_{00}$", "$C_{01}$", "$C_{02}$", "$C_{10}$", "$C_{11}$", "$C_{12}$", "$C_{20}$", "$C_{21}$", and "$C_{22}$") are predetermined in shipping from the factory. In a second embodiment, the set color correction coefficients are determined in the calibration. An endoscope system according to the second embodiment has a second calibration mode for determining the color correction coefficients to be used in the color correction matrix process, in addition to the normal observation mode, the special observation mode, and the first calibration mode.

According to the second embodiment, in the second calibration mode, each of the LEDs 20a to 20d is emitted at a second light emission ratio (the violet light V:the blue light B:the green light G:the red light R) under the control of the light source controller 21, and the image sensor 48 captures images based on the light emission, as described below. First, each of four types of monochrome light including the violet light V (at a second light emission ratio of 1:0:0:0), the blue light B (at a second light emission ratio of 0:1:0:0), the green light G (at a second light emission ratio of 0:0:1:0), and the red light R (at a second light emission ratio of 0:0:0:1) is applied to the reference object RO. Whenever each type of monochrome light is applied, the image sensor 48 outputs signals of three colors i.e. an R image signal, a G image signal, and a B image signal. Thereby, during the application of the monochrome light, the twelve image signals (the application of the four types of light×the image signals of the three colors) are obtained in total.

Next, two-color mixed light in which light of two colors is combined out of the violet light V, the blue light B, the green light G, and the red light R (for example, in the case of emitting the violet light V and the blue light B, the second light emission ratio is set at 1:1:0:0) is applied. In other words, each of six types of mixed light is applied, and the image sensor 48 outputs the image signals of the three colors, i.e. the R image signal, the G image signal, and the B image signal whenever each type of mixed light is applied. Thereby, the eighteen image signals (the application of the six types of light×the image signals of the three colors) are obtained in total during the application of the two-color mixed light. Also, three-color mixed light in which light of three colors is combined out of the violet light V, the blue light B, the green light G, and the red light R (for example, in the case of emitting the violet light V, the blue light B, and the green light G, the second light emission ratio is set at 1:1:1:0) is applied. In other words, each of three types of mixed light is applied, and the image sensor 48 outputs the image signals of the three colors, i.e. the R image signal, the G image signal, and the B image signal whenever each type of mixed light is applied. Thereby, the nine image signals (the application of the three types of light×the image signals of the three colors) are obtained in total during the application of the three-color mixed light.

At last, imaging is performed under application of the normal light by turning on all of the LEDs, and imaging is performed with turning off all the LEDs. Thereby, the image signals of the three colors, that is, the R image signals, the G image signals, and the B image signals are outputted from the image sensor 48. Thus, the six image signals (the image signals of the three colors obtained during turning on all the LEDs+the image signals of the three colors obtained during turning off all the LEDs) are obtained in total. As described above, the forty-five image signals are obtained in total.

Figure 8:
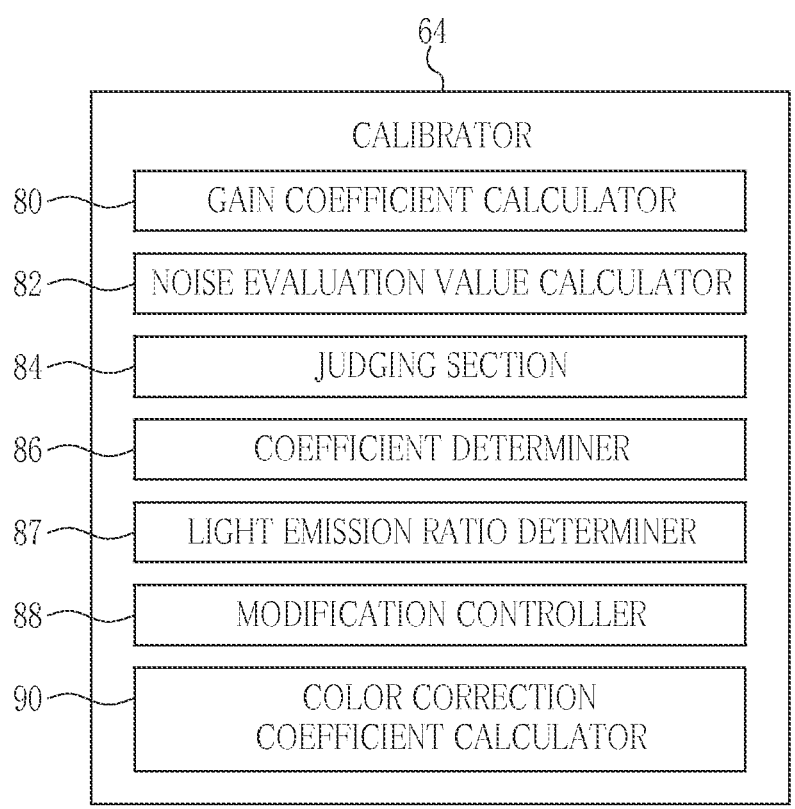
FIG. 8 is a block diagram of a calibrator according to a second embodiment.

As shown in FIG. 8, a color correction coefficient calculator 90 provided in the calibrator 64 calculates the set color correction coefficients ("$C_{00}$", "$C_{01}$", "$C_{02}$", "$C_{10}$", "$C_{11}$", "$C_{12}$", "$C_{20}$", "$C_{21}$", and "$C_{22}$") based on the forty-five image signals obtained as described above and forty-five image signals to be targets. Note that, the set color correction coefficients are calculated by using the forty-five image signals, but the number of the used image signals may be more than or less than forty-five.

The present invention will be further concretely described in the following practical example and comparative examples.

Practical Example 1

The reference object RO was imaged under application of the violet light V, the blue light B, the green light G, and the red light R from the V-LED 20a, the B-LED 20b, the G-LED 20c, and the R-LED 20d, respectively. The imaging of the reference object RO was performed by the color image sensor 48 (the image sensor having the spectral characteristics of FIG. 5) having the G pixels that were sensitive to the blue light B and the red light R in addition to the green light G. The calibrator 64 determined the set light emission ratios and the set gain coefficients of the violet light V, the blue light B, the green light G, and the red light R such that the noise evaluation value came to be the allowance or less. Also, the color correction coefficient calculator 90 calculated the set color correction coefficients.

Then, an Rc noise representing an amplification amount of noise in the R image signal caused by the set color correction coefficients and an Rt noise representing an amplification amount of noise in the R image signal caused by the set gain coefficients and the set color correction coefficients were calculated according to the following expressions (6) and (7).

$$Rc\text{ noise} = \sqrt{(C_{00})^2 + (C_{01})^2 + (C_{02})^2} \quad \text{Expression (6):}$$

$$Rt\text{ noise} = \sqrt{(C_{00}\times\text{Gain}R)^2 + (C_{01}\times\text{Gain}G)^2 + (C_{02}\times\text{Gain}B)^2} \quad \text{Expression (7):}$$

In a like manner, a Gc noise representing an amplification amount of noise in the G image signal caused by the set color correction coefficients and a Gt noise representing an amplification amount of noise in the G image signal caused by the set gain coefficients and the set color correction coefficients were calculated according to the following expressions (8) and (9). Also, a Bc noise representing an amplification amount of noise in the B image signal caused by the set color correction coefficients and a Bt noise representing an amplification amount of noise in the B image signal caused by the set gain coefficients and the set color correction coefficients were calculated according to the following expressions (10) and (11).

$$Gc\ \text{noise} = \sqrt{(C_{10})^2 + (C_{11})^2 + (C_{12})^2}$$ Expression (8):

$$Gt\ \text{noise} = \sqrt{(C_{10} \times \text{GainR})^2 + (C_{11} \times \text{GainG})^2 + (C_{12} \times \text{GainB})^2}$$ Expression (9):

$$Bc\ \text{noise} = \sqrt{(C_{20})^2 + (C_{21})^2 + (C_{22})^2}$$ Expression (10):

$$Bt\ \text{noise} = \sqrt{(C_{20} \times \text{GainR})^2 + (C_{21} \times \text{GainG})^2 + (C_{22} \times \text{GainB})^2}$$ Expression (11):

Furthermore, a luminance noise Lc representing an amplification amount of noise in the RGB image signal caused by the set color correction coefficients and a luminance noise Lt caused by the set gain coefficients and the set color correction coefficients were calculated. Note that, the luminance noise Lc, which corresponds to a value converted to the luminance amplification factor, can be calculated from the above expression (3). The luminance noise Lt, which corresponds to a value converted to the sum of the RGB amplification factors, can be calculated from the above expression (4).

Table 1 shows practical results of the practical example 1.

TABLE 1

| GainR | GainG | GainB | 1.25 | 1.00 | 1.24 |
|---|---|---|---|---|---|
| $C_{00}$ | $C_{01}$ | $C_{02}$ | 1.18 | 0.00 | -0.29 |
| $C_{10}$ | $C_{11}$ | $C_{12}$ | -0.32 | 1.68 | -0.37 |
| $C_{20}$ | $C_{21}$ | $C_{22}$ | -0.13 | 0.00 | 1.08 |
| $C_{00}$*GainR | $C_{01}$*GainG | $C_{02}$*GainB | 1.46 | 0.00 | -0.36 |
| $C_{10}$*GainR | $C_{11}$*GainG | $C_{12}$*GainB | -0.40 | 1.68 | -0.46 |
| $C_{20}$*GainR | $C_{21}$*GainG | $C_{22}$*GainB | -0.16 | 0.00 | 1.33 |
| Rc | Rt | | 1.21 | 1.51 | |
| Gc | Gt | | 1.75 | 1.78 | |
| Bc | Bt | | 1.09 | 1.34 | |
| Lc | Lt | | 1.52 | 1.66 | |

In Table 1, "Rc" represents the Rc noise, and "Rt" represents the Rt noise. "Gc" represents the Gc noise, and "Gt" represents the Gt noise. "Bc" represents the Bc noise, and "Bt" represents the Bt noise. Also, "Lc" represents the luminance noise Lc, and "Lt" represents the luminance noise Lt. These notations are the same in Tables 2 to 4 shown below.

Comparative Example 1

The reference object RO was imaged under application of the violet light V, the blue light B, the green light G, and the red light R from the V-LED 20a, the B-LED 20b, the G-LED 20c, and the R-LED 20d, respectively. The imaging of the reference object RO was performed by the color image sensor 48 (the image sensor having the spectral characteristics of FIG. 5) having the G pixels that were sensitive to the blue light B and the red light R in addition to the green light G. The light emission ratio of the violet light V, the blue light B, the green light G, and the red light R was adjusted in a state of setting every gain coefficient "Gain R", "Gain G", and "Gain B" at 1, so that the ratio among the R image signal, the G image signal, and the B image signal became 1:1:1. Also, the set color correction coefficients were calculated in the same method as the color correction coefficient calculator 90. As with the practical example 1, were calculated the Rc noise, the Rt noise, the Gc noise, the Gt noise, the Bc noise, the Bt noise, the luminance noise Lc, and the luminance noise Lt.

Table 2 shows practical results of a comparative example 1.

TABLE 2

| GainR | GainG | GainB | 1.00 | 1.00 | 1.00 |
|---|---|---|---|---|---|
| $C_{00}$ | $C_{01}$ | $C_{02}$ | 0.94 | 0.31 | -0.37 |
| $C_{10}$ | $C_{11}$ | $C_{12}$ | -0.69 | 2.31 | -0.64 |
| $C_{20}$ | $C_{21}$ | $C_{22}$ | -0.21 | 0.23 | 0.93 |
| $C_{00}$*GainR | $C_{01}$*GainG | $C_{02}$*GainB | 0.94 | 0.31 | -0.37 |
| $C_{10}$*GainR | $C_{11}$*GainG | $C_{12}$*GainB | -0.69 | 2.31 | -0.64 |
| $C_{20}$*GainR | $C_{21}$*GainG | $C_{22}$*GainB | -0.21 | 0.23 | 0.93 |
| Rc | Rt | | 1.06 | 1.06 | |
| Gc | Gt | | 2.49 | 2.50 | |
| Bc | Bt | | 0.98 | 0.98 | |
| Lc | Lt | | 1.91 | 1.91 | |

Comparative Example 2

The reference object RO was imaged under application of the violet light V, the blue light B, the green light G, and the red light R at a predetermined light emission ratio from the V-LED 20a, the B-LED 20b, the G-LED 20c, and the R-LED 20d, respectively. The imaging of the reference object RO was performed by the color image sensor 48 (the image sensor having the spectral characteristics of FIG. 5) having the G pixels that were sensitive to the blue light B and the red light R in addition to the green light G. The gain coefficients "Gain R", "Gain G", and "Gain B" were adjusted such that the ratio among the R image signal, the G image signal, and the B image signal became 1:1:1. Also, the set color correction coefficients were calculated in the same method as the color correction coefficient calculator 90. As with the practical example 1, were calculated the Rc noise, the Rt noise, the Gc noise, the Gt noise, the Bc noise, the Bt noise, the luminance noise Lc, and the luminance noise Lt.

Table 3 shows practical results of a comparative example 2.

TABLE 3

| GainR | GainG | GainB | 1.68 | 1.00 | 1.64 |
|---|---|---|---|---|---|
| $C_{00}$ | $C_{01}$ | $C_{02}$ | 1.59 | -0.48 | -0.23 |
| $C_{10}$ | $C_{11}$ | $C_{12}$ | -0.05 | 1.23 | -0.19 |
| $C_{20}$ | $C_{21}$ | $C_{22}$ | -0.07 | -0.29 | 1.31 |
| $C_{00}$*GainR | $C_{01}$*GainG | $C_{02}$*GainB | 2.67 | -0.48 | -0.37 |
| $C_{10}$*GainR | $C_{11}$*GainG | $C_{12}$*GainB | -0.08 | 1.23 | -0.31 |
| $C_{20}$*GainR | $C_{21}$*GainG | $C_{22}$*GainB | -0.12 | -0.29 | 2.16 |
| Rc | Rt | | 1.68 | 2.74 | |
| Gc | Gt | | 1.24 | 1.27 | |
| Bc | Bt | | 1.35 | 2.18 | |
| Lc | Lt | | 1.38 | 1.80 | |

Comparative Example 3

The reference object RO was imaged under application of white light (light including at least visible light of 400 to 700 nm) from a xenon lamp. The imaging of the reference object RO was performed by the color image sensor 48 (the image sensor having the spectral characteristics of FIG. 5) having the G pixels that were sensitive to the blue light B and the red light R in addition to the green light G. The gain coefficients "Gain R", "Gain G", and "Gain B" were adjusted such that the ratio among the R image signal, the G image signal, and the B image signal became 1:1:1. Also, the set color correction coefficients were calculated in the same method as the color correction coefficient calculator 90. As with the practical example 1, were calculated the Rc noise, the Rt noise, the Gc noise, the Gt noise, the Bc noise, the Bt noise, the luminance noise Lc, and the luminance noise Lt.

Table 4 shows practical results of a comparative example 3.

TABLE 4

| | | | | | |
|---|---|---|---|---|---|
| GainR | GainG | GainB | 1.40 | 1.00 | 1.57 |
| $C_{00}$ | $C_{01}$ | $C_{02}$ | 1.25 | −0.08 | −0.29 |
| $C_{10}$ | $C_{11}$ | $C_{12}$ | −0.26 | 1.59 | −0.34 |
| $C_{20}$ | $C_{21}$ | $C_{22}$ | −0.07 | −0.35 | 1.37 |
| $C_{00}$*GainR | $C_{01}$*GainG | $C_{02}$*GainB | 1.74 | −0.08 | −0.45 |
| $C_{10}$*GainR | $C_{11}$*GainG | $C_{12}$*GainB | −0.36 | 1.59 | −0.54 |
| $C_{20}$*GainR | $C_{21}$*GainG | $C_{22}$*GainB | −0.10 | −0.35 | 2.15 |
| Rc | Rt | | 1.28 | 1.80 | |
| Gc | Gt | | 1.64 | 1.71 | |
| Bc | Bt | | 1.42 | 2.18 | |
| Lc | Lt | | 1.51 | 1.79 | |

According to the practical example 1, as compared with the comparative example 1, the set gain coefficients are slightly high but the set color correction coefficients stay at a low level on the whole. Thus, according to the practical example 1, out of the noises, the luminance noise Lt is smaller than that of the comparative examples 1 to 3. On the contrary, according to the comparative example 1, as compared with the practical example 1, the set color correction coefficients related to the G image signal are especially high, though the set gain coefficients are small. Thus, in the comparative example 1, the Gc noise and the Gt noise are higher than that of the practical example 1 and the comparative examples 2 and 3. According to the comparative examples 2 and 3, the set gain coefficients "Gain R" and "Gain B" are high as compared with the practical example 1 and the comparative example 1. Thus, in the comparative examples 2 and 3, the Rc noise, the Rt noise, the Bc noise, and the Bt noise are higher than those of the practical example 1 and the comparative example 1.

Note that, as the image sensor 48, a so-called complementary color image sensor having complementary color filters of C (cyan), M (magenta), Y (yellow), and G (green) may be used instead of the RGB color image sensor. In the case of using the complementary color image sensor outputting an image signal of four colors of CMYG, it is required to convert the image signal of the four colors of CMYG into the image signal of the three colors of RGB by a complementary color-to-primary color conversion based on the following expression (12). Then, the set light emission ratios, the set gain coefficients, and the like are determined in the same manner as the above embodiment based on the RGB three-color image signal converted by the complementary color-to-primary color conversion.

$$\begin{bmatrix} R \\ G \\ B \end{bmatrix} = \begin{bmatrix} k_{11} & k_{12} & k_{13} & k_{14} \\ k_{21} & k_{22} & k_{23} & k_{24} \\ k_{31} & k_{32} & k_{33} & k_{34} \end{bmatrix} \times \begin{bmatrix} Cy \\ Mg \\ G \\ Ye \end{bmatrix}$$ Expression (12)

Note that, in the expression (12), "$k_{11}$", "$k_{12}$", "$k_{13}$", "$k_{14}$", "$k_{21}$", "$k_{22}$", "$k_{23}$", "$k_{24}$", "$k_{31}$", "$k_{32}$", "$k_{33}$", and "$k_{34}$" represent conversion coefficients for converting the CMYG image signal into the RGB image signal. As is apparent from the expression (12), for example, the G image signal contains not only a signal outputted from G pixels of the complementary color image sensor but also three other signals, that is, a signal outputted from Cy pixels of the complementary color image sensor is multiplied by "$k_{21}$", a signal outputted from Mg pixels thereof is multiplied by "$k_{22}$", and a signal outputted from Ye pixels thereof is multiplied by "$k_{24}$". Accordingly, the G image signal after the conversion includes information about light in a band other than the green band.

Figure 9:
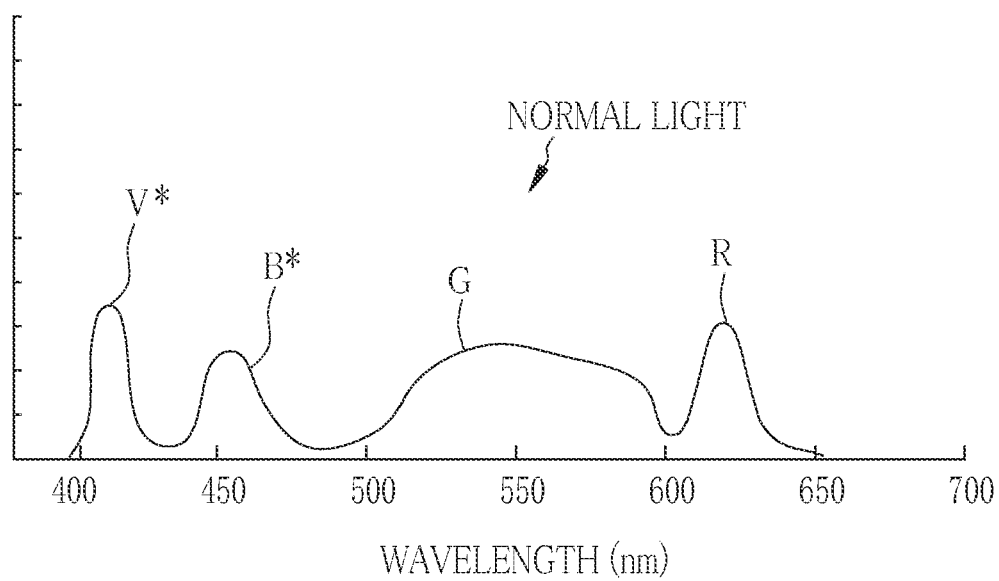
FIG. 9 is a graph showing an emission spectrum of normal light different from FIG. 3.
Figure 10:
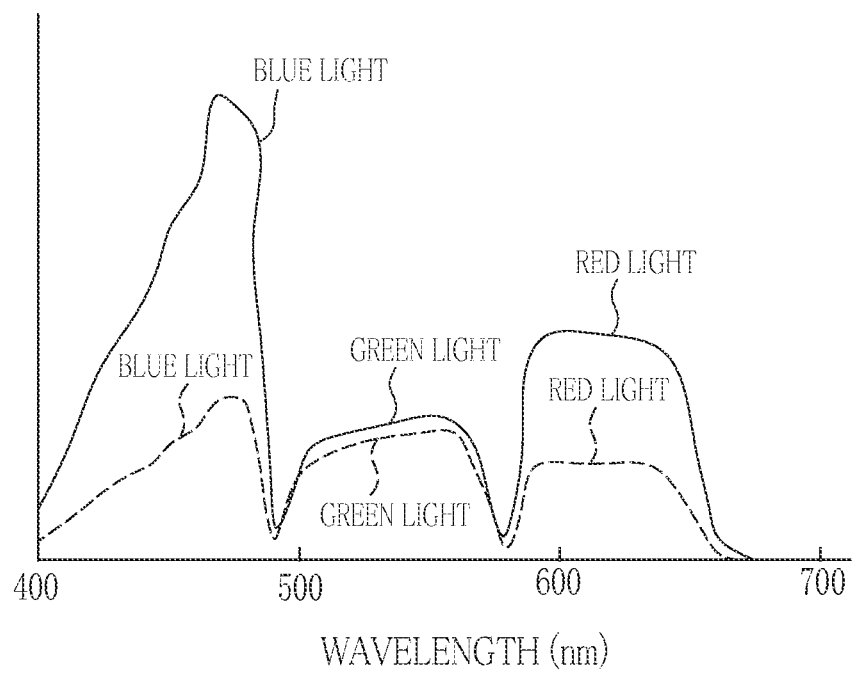
FIG. 10 is a graph showing the relative radiation intensity of blue light, green light, and red light after adjustment of white balance by light amount control, and the relative radiation intensity of default (initial setting) blue light, green light, and red light.

Note that, the light of the four colors having the light emission spectrum of FIG. 3 is used in the above embodiments, but the light emission spectrum is not limited to this. For example, as shown in FIG. 9, the light may include violet light V* that has a center wavelength of 410 to 420 nm and a wavelength range on a slightly longer wavelength side than the violet light V of FIG. 3, in addition to the green light G and the red light R having the same spectra as FIG. 3. Also, blue light B* may have a center wavelength of 445 to 460 nm and a wavelength range on a slightly shorter wavelength side than the blue light B of FIG. 3.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   a light source unit for emitting multi-colored light having a set light emission ratio in a specific observation mode;
   a processing circuitry configured for:
   performing a color correction matrix process by using a set color correction coefficient;
   performing a white balance process by using a set gain coefficient; and
   determining said set light emission ratio and said set gain coefficient such that a noise evaluation value calculated based on said set color correction coefficient and said set gain coefficient becomes an allowance or less,
   said endoscope system further comprising:
   an endoscope having a color image sensor for imaging an object and outputting a multi-colored image signal; and
   image signal storage for storing a first multi-colored image signal obtained by imaging with said color image sensor a reference object irradiated with said multi-colored light having said first light emission ratio,
   said processing circuitry further configured for:
   controlling the amount of light of each color so that said multi-colored light has a first light emission ratio;
   calculating a provisional gain coefficient based on said first multi-colored image signal;
   calculating said noise evaluation value based on said provisional gain coefficient and said set color correction coefficient;
   judging whether or not said noise evaluation value is said allowance or less;
   determining said provisional gain coefficient used in calculating said noise evaluation value that is judged to be said allowance or less, as said set gain coefficient; and
   determining said first light emission ratio of said multi-colored light used in calculating said noise evaluation value that is judged to be said allowance or less, as said set light emission ratio.

2. The endoscope system according to claim 1, wherein said processing circuitry is further configured for:
   modifying said first light emission ratio of said multi-colored light and calculating said provisional gain coefficient and said noise evaluation value from said first multi-colored image signal obtained based on said modified first light emission ratio in a case where said noise evaluation value is judged to exceed said allowance.

3. The endoscope system according to claim 1, wherein said noise evaluation value increases with increase in said provisional gain coefficient or said set color correction coefficient.

4. The endoscope system according to claim 1, wherein said multi-colored light includes red light, green light, and blue light, and said multi-colored image signal is an RGB image signal.

5. The endoscope system according to claim 1, wherein said multi-colored light includes first narrow band light in a violet band or a blue band and second narrow band light in a green band, and said multi-colored image signal is an RGB image signal.

6. The endoscope system according to claim 4, wherein out of said RGB image signal, a G image signal has information about light in a band other than a green band of said multi-colored light.

7. The endoscope system according to claim 1, wherein said processing circuitry is further configured for:
controlling the amount of light of each color so that said multi-colored light has a second light emission ratio; and
calculating said set color correction coefficient from a second multi-colored image signal obtained by imaging with said color image sensor said reference object irradiated with said multi-colored light having said second light emission ratio.

8. A method for operating an endoscope system comprising the steps of:
emitting multi-colored light having a set light emission ratio from a light source unit in a specific observation mode;
performing a color correction matrix process by a processing circuitry by using a set color correction coefficient;
determining said set light emission ratio by said processing circuitry such that a noise evaluation value calculated based on at least said set color correction coefficient becomes an allowance or less,
wherein said processing circuitry determines a set gain coefficient to be used in a white balance process, such that said noise evaluation value becomes said allowance or less;
controlling the amount of light of each color so that said multi-colored light has a first light emission ratio;
storing to image signal storage a first multi-colored image signal obtained by imaging with a color image sensor a reference object irradiated with said multi-colored light having said first light emission ratio;
calculating a provisional gain coefficient from said first multi-colored image signal;
calculating a noise evaluation value based on said provisional gain coefficient and said set color correction coefficient:
judging whether or not said noise evaluation value is said allowance or less;
determining said provisional gain coefficient used in calculating said noise evaluation value that is judged to be said allowance or less, as said set gain coefficient; and
determining said first light emission ratio of said multi-colored light used in calculating said noise evaluation value that is judged to be said allowance or less, as said set light emission ratio.

* * * * *